US00PP20321P2

(12) United States Plant Patent
Miedema-Jorna

(10) Patent No.: US PP20,321 P2
(45) Date of Patent: Sep. 15, 2009

(54) ***PETUNIA* PLANT NAMED 'FORT IMPROBURGPIC'**

(50) Latin Name: *Petunia×hybrida*
Varietal Denomination: Fort Improburgpic

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/220,695

(22) Filed: Jul. 25, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'Fort Improburgpic', characterized by its upright to outwardly spreading and mounded growth habit; freely branching habit; freely flowering habit; large dark purple-colored flowers with white-colored margins; and good garden performance.

1 Drawing Sheet

Botanical designation: *Petunia×hybrida.*
Cultivar denomination: 'FORT IMPROBURGPIC'.

BACKGROUND OF THE INVENTION

The present invention relates to a new and distinct cultivar of *Petunia,* botanically known as *Petunia×hybrida* and hereinafter referred to by the name 'Fort Improburgpic'.

The new *Petunia* is a naturally-occurring whole plant mutation of *Petunia×hybrida* 'Fortunia Burgundy Picotee', not patented. The new *Petunia* was discovered and selected by the Inventor as a single flowering plant from within a population of plants of 'Fortunia Burgundy Picotee' in a controlled greenhouse environment in De Lier, The Netherlands in 2006.

Asexual reproduction of the new *Petunia* by terminal cuttings in a controlled greenhouse environment in De Lier, The Netherlands since 2007, has shown that the unique features of this new *Petunia* are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fort Improburgpic'. These characteristics in combination distinguish 'Fort Improburgpic' as a new and distinct cultivar of *Petunia:*

1. Upright to outwardly spreading and mounded growth habit.
2. Freely branching habit.
3. Freely flowering habit.
4. Large dark purple-colored flowers with white-colored margins.
5. Good garden performance.

Plants of the new *Petunia* can be compared to plants of the parent, 'Fort Burgundy Picotee'. Plants of the new *Petunia* differ from plants of 'Fort Burgundy Picotee' primarily in flower color as plants of 'Fort Burgundy Picotee' have a smaller and less pronounced white-colored margin.

Plants of the new *Petunia* can be compared to plants of *Petunia×hybrida* 'Sophia', not patented. In side-by-side comparisons conducted in De Lier, The Netherlands, plants of the new *Petunia* differed from plants of 'Sophia' primarily in flower color as plants of 'Sophia' had lighter purple-colored flowers.

BRIEF DESCRIPTION OF THE PHOTOGRAPH

The accompanying colored photograph illustrates the overall appearance of the new *Petunia,* showing the colors as true as it is reasonably possible to obtain in colored reproductions of this type. Colors in the photograph may differ slightly from the color values cited in the detailed botanical description which accurately describe the colors of the new *Petunia.* The photograph comprises a side perspective view of a typical flowering plant of 'Fort Improburgpic' grown in a container.

DETAILED BOTANICAL DESCRIPTION

The aforementioned photograph and following observations, measurements and values describe plants grown in De Lier, The Netherlands, under commercial practice during the spring and early summer in a glass-covered greenhouse with day and night temperatures averaging 18° C. Rooted young plants had been growing for twelve weeks when the photograph and description were taken. Plants used for the description were grown in 10.5-cm containers. In the following description, color references are made to The Royal Horticultural Society Colour Chart, 2001 Edition, except where general terms of ordinary dictionary significance are used.

Botanical classification: *Petunia×hybrida* 'Fort Improburgpic'.

Parentage: Naturally-occurring whole plant mutation of *Petunia×hybrida* 'Fortunia Burgundy Picotee', not patented.

Propagation:

*Type.*—By terminal cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About two to three weeks at temperatures of 19° C. to 20° C.

*Root description.*—Fine; white in color.

*Rooting habit.*—Freely branching; moderately dense.

Plant description:

*Plant and growth habit.*—Upright to outwardly spreading and mounding growth habit. Freely branching habit with about eight primary lateral branches each with multiple secondary lateral branches; pinching is typically not required. Moderately vigorous growth habit.

*Plant height.*—About 14 cm.

*Plant diameter.*—About 37 cm.

Lateral branch description:

*Length.*—About 14 cm.

*Diameter.*—About 4 mm.

*Internode length.*—About 2.5 mm to 3 mm.

*Strength.*—Moderately strong.

*Aspect.*—Initially upright to outwardly spreading.

*Texture.*—Densely pubescent; viscid.

*Color.*—Close to 144B.

Leaf description:

*Arrangement.*—Alternate, simple; sessile.

*Length.*—About 4.5 cm.

*Width.*—About 2.5 cm.

*Shape.*—Ovate.

*Apex.*—Acute.

*Base.*—Attenuate.

*Margin.*—Entire.

*Texture, upper and lower surfaces.*—Densely pubescent; viscid.

*Venation pattern.*—Pinnate; arcuate.

*Color.*—Developing leaves, upper surface: Close to 143A. Developing leaves, lower surface: Close to 143C. Fully expanded leaves, upper surface: Close to 138A; venation, close to 143A to 143B. Fully expanded leaves, lower surface: Close to 138B; venation, close to 143C to 143D.

Flower description:

*Flower arrangement and habit.*—Relatively large salverform flowers arranged singly arising from leaf axils. Freely flowering habit with usually about 60 flowers developing per plant. Flowers not persistent. Flowers face upright to outwardly.

*Fragrance.*—None detected.

*Natural flowering season.*—Plants flower continuously from spring into the autumn in The Netherlands. Plants typically beginning flowering about 6.5 weeks after planting.

*Flower longevity.*—Individual flowers last about five days on the plant. Flowers persistent.

*Flower diameter.*—About 7 cm.

*Flower length* (*height*).—About 5 cm.

*Throat diameter.*—About 1.2 cm.

*Tube length.*—About 2.5 cm.

*Tube diameter, base.*—About 5 mm.

*Flower bud.*—Shape: Narrowly oblanceolate. Length: About 2.9 cm. Diameter: About 6 mm. Color: Close to 144B overlain with close to 59A.

*Corolla.*—Arrangement: Five petals fused at the base and opening into a flared trumpet. Petal length from throat: About 5.5 cm. Petal lobe width: About 2.9 cm. Petal shape: Spatulate. Petal apex: Retuse. Petal margin: Entire. Petal lobe texture, upper and lower surfaces: Smooth, glabrous; satiny. Throat texture: Smooth, glabrous. Tube texture: Densely pubescent. Color: Petal, when opening and fully opened, upper surface: Close to 59A; towards the margin, close to 155D; venation, similar to lamina. Center color becoming closer to 83A to 83B with development. Petal, when opening and fully opened, lower surface: Close to 59A; towards the margin, close to 155D; venation, close to 144A or 59B. Throat: Close to 59A; venation, close to 59A. Tube: Close to 59B; venation, close to 59B.

*Calyx.*—Arrangement: One star-shaped calyx tube with five sepals fused at the base per flower. Sepal length: About 1.8 cm. Sepal width: About 5 mm. Sepal shape: Narrowly oblong. Sepal apex: Acute. Sepal base: Cuneate. Sepal margin: Entire. Sepal texture, upper and lower surfaces: Densely pubescent; viscid. Color, immature and mature, upper surface: Close to 143A. Color, immature and mature, lower surface: Close to 143B.

*Peduncles.*—Length: About 4 cm. Diameter: About 2 mm. Angle: Erect to about 40° from stem axis. Strength: Moderately strong. Texture: Densely pubescent; viscid. Color: Close to 144B.

*Reproductive organs.*—Stamens: Quantity per flower: Five. Filament length: About 2.1 cm. Filament color: Close to 157D. Anther shape: Broadly reniform. Anther length: About 2 mm. Anther color: Close to 155A to 155B. Pollen amount: Moderate. Pollen color: Close to NN155A. Pistils: Quantity per flower: One. Pistil length: About 2 cm. Style length: About 2 cm. Style color: Close to 144A. Stigma shape: Flattened, three-lobed. Stigma color: Close to 144A. Ovary color: Close to 144C.

*Fruit/seeds.*—Fruit and seed development have not been observed on plants of the new *Petunia*.

Garden performance: Plants of the new *Petunia* have been observed to have good garden performance and tolerate wind, rain and temperatures ranging from about 5° C. about 35° C.

Pathogen/pest resistance: Plants of the new *Petunia* have not been observed to be resistant to pathogens and pests common to *Petunia*.

It is claimed:

1. A new and distinct *Petunia* plant named 'Fort Improburgpic' as illustrated and described.

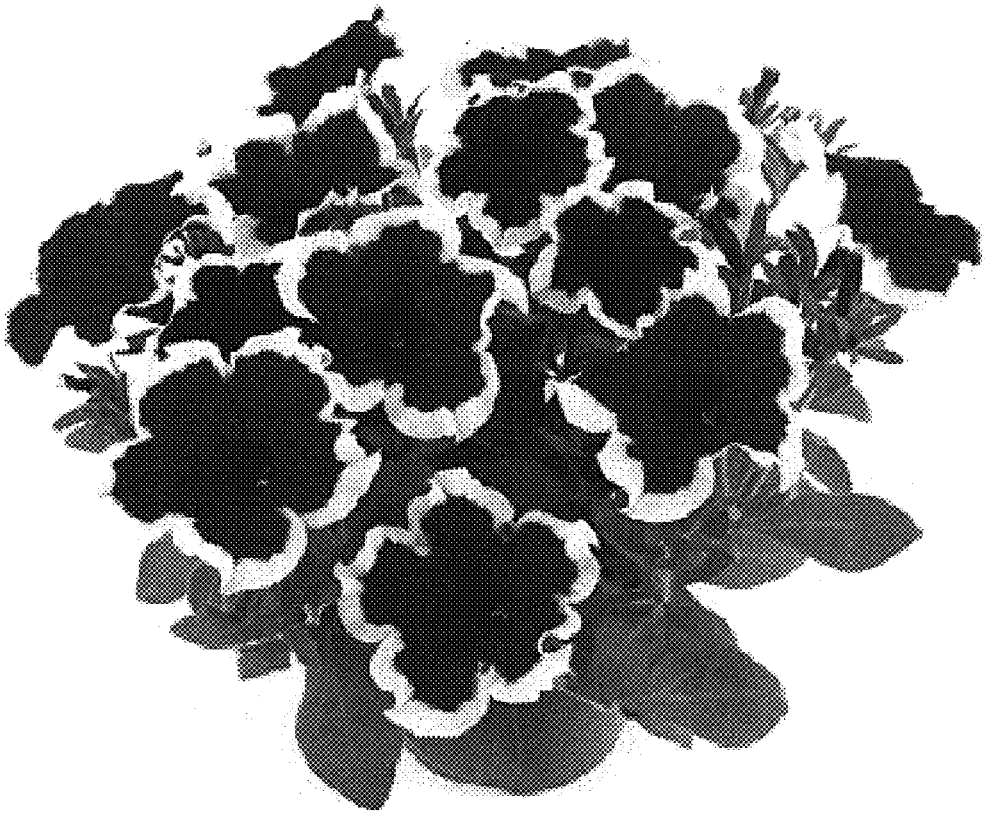

* * * * *